United States Patent
Schenck Zu Schweinsberg et al.

(10) Patent No.: US 7,793,536 B2
(45) Date of Patent: Sep. 14, 2010

(54) METHOD TO DETERMINE THE COMPOSITION OF A FUEL MIXTURE

(75) Inventors: Alexander Schenck Zu Schweinsberg, Meolingen (DE); Corren Heimgaertner, Stuttgart (DE); Klaus Ries-Mueller, Bad Rappenau (DE)

(73) Assignee: Robert Bosch GmbH, Stuttgart (DE)

( * ) Notice: Subject to any disclaimer, the term of this patent is extended or adjusted under 35 U.S.C. 154(b) by 298 days.

(21) Appl. No.: 12/126,086

(22) Filed: May 23, 2008

(65) Prior Publication Data
US 2008/0289405 A1   Nov. 27, 2008

(30) Foreign Application Priority Data
May 23, 2007   (DE)   ................ 10 2007 023 899

(51) Int. Cl.
*G01M 15/08*   (2006.01)
(52) U.S. Cl. .................................. 73/114.55
(58) Field of Classification Search ............. 73/114.16, 73/114.38, 114.55, 114.56
See application file for complete search history.

(56) References Cited

U.S. PATENT DOCUMENTS 7,628,062 B2 * 12/2009 Healy et al. ............... 73/114.55

| | | |
|---|---|---|
| 2002/0083927 A1 | 7/2002 | Bayerle et al. |
| 2008/0289401 A1 * | 11/2008 | Boerkel ................ 73/61.47 |
| 2009/0064682 A1 * | 3/2009 | Healy et al. ............ 60/772 |
| 2009/0223485 A1 * | 9/2009 | Hamedovic et al. ...... 123/435 |

FOREIGN PATENT DOCUMENTS

DE   41 17 440   5/1991

* cited by examiner

*Primary Examiner*—Eric S McCall
(74) *Attorney, Agent, or Firm*—Merchant & Gould P.C.

(57) ABSTRACT

The invention concerns a method to determine the composition of a fuel mixture from a first and at least a second fuel for the operation of an internal combustion engine with at least one combustion chamber, wherein the first and the second fuel have different boiling points and/or different enthalpies of evaporation. Provision is thereby made for the composition of the fuel mixture to be ascertained from the pressure in the combustion chamber and/or a parameter associated with the pressure and/or the time history of the pressure and/or the time history of a parameter associated with the pressure during and/or after an injection of fuel during a compression phase of the fuel-air mixture. An advantage of the method according to the invention is that when initially starting the engine after filling the tank (fueling), the fuel mixture ratio, which resulted from the filling of the tank (fueling), can already hereby be determined.

15 Claims, 1 Drawing Sheet

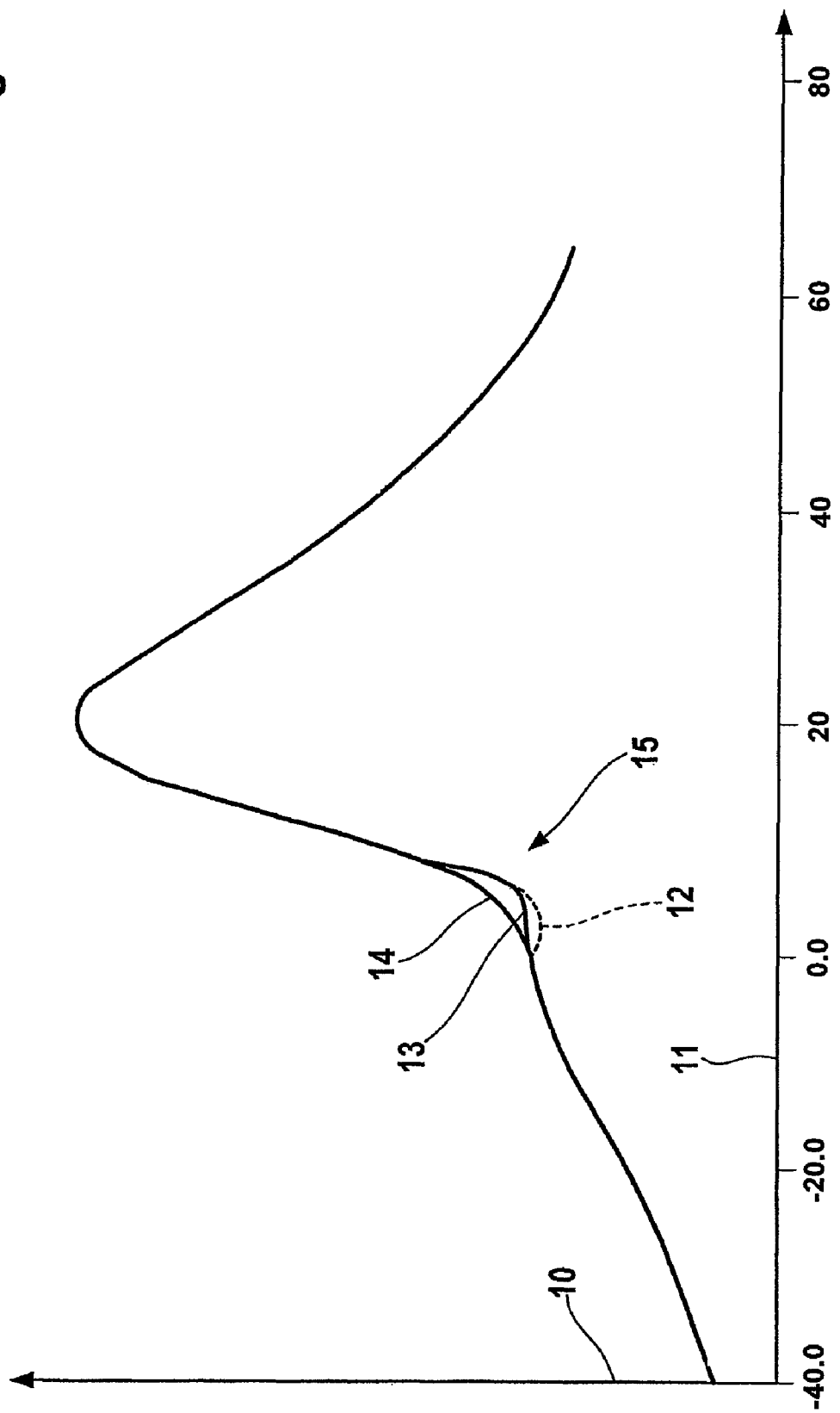

METHOD TO DETERMINE THE COMPOSITION OF A FUEL MIXTURE

TECHNICAL FIELD

The invention concerns a method to determine the composition of a fuel mixture from a first and at least a second fuel for the operation of an internal combustion engine with at least one combustion chamber, wherein the first and the second fuel have different boiling points and/or different enthalpies of evaporation.

BACKGROUND

Internal combustion engines on the basis of gasoline engines are generally operated with fuel from hydrocarbons, from fossil fuels based on refined crude oil. Ethanol produced from renewable resources (plants) or another kind of alcohol is increasingly being added in various mixing ratios to the fuel. In the USA and Europe a mixture of 70-85% ethanol and 15-30% gasoline is often distributed under the trade name E85. The internal combustion engines are designed in such a way that they can be operated with pure gasoline as well as with mixtures up to E85. This is denoted as a "flex-fuel operation". The operating parameters in the flex-fuel operations have to be adapted to the respectively existing fuel mixture for an efficient operation with only a small discharge of toxic emissions, while at the same time a high degree of engine performance is maintained. A stoichiometric fuel-air mixture ratio is, for example, present at 14.7 volumetric parts of air per part of gasoline; however, when using ethanol, a proportion of air of 9 volumetric parts must be set. Small and/or slow changes in the ethanol content can be detected and taken into account by the engine management system of the internal combustion engine by means of a lambda probe and/or a knock sensor. Rapid changes with a significant deviation in the composition of the fuel mixture can also occur, for example, after filling the tank (fueling). If the internal combustion engine were operated with 100% gasoline and filled with E85 when the tank was close to empty, problems in starting and disturbances in the combustion can arise, which can also increase the harmful exhaust gas emissions. According to the state of the art, such rapid changes in the composition of the fuel can be detected using an ethanol sensor. This component, however, increases the cost of the internal combustion engine.

A method is known from the German patent DE 4117440 C2 for the adaptive adjustment of a fuel-air mixture to take into account fuel characteristics in the operation of an internal combustion engine, which has a lambda controller, which transmits a control factor RF, and which has an adaptation integrator, which transmits an adaptation factor AF with a variable adaptation speed. Beside the control factor RF, said adaptation factor AF influences the adjustment of the fuel-air mixture. Provision is thereby made for a test to determine if the lambda control deviation amplitude exceeds an initial threshold value. If this is the case, the adaptation speed is set to an increased value until a specified condition is filled, whereby the controller switches back to a base adaptation speed.

The method makes it possible to operate internal combustion engines, which can be operated with different fuels, trouble-free. Thus, the injection time must, for example, be lengthened by more than 20% in order to maintain the same lambda values in the exhaust gas, when a change is made from pure gasoline to a fuel mixture with 85% ethanol and 15% gasoline. According to the method described in the text of the German patent DE 4117440 C2, an appropriate adaptation intervention is performed for this purpose. Because a very large correction in the injection times and consequently in the adaptation intervention must be undertaken when a change in fuel occurs in comparison to the compensation for factors of wear and manufacture, the adaptation speed is significantly increased in the proposed method when a change in fuel is detected.

The fuel mixture ratio can be determined on the basis of the adjusted adaptation value. Despite the increased adaptation speed, the method requires a sufficiently long settling time. If a significant change in the fuel mixture ratio is caused by a filling of the tank (fueling), this can lead to problems in starting and misfires, which successively lead to an increase in exhaust gas emissions.

It is the task of the invention to provide a method, which allows for a fast and cost effective detection of the composition of a fuel mixture from fuels with different boiling points and/or enthalpies of evaporation.

SUMMARY

The task of the invention is thereby solved, in that the composition of the fuel mixture is ascertained from the pressure in the combustion chamber and/or a parameter associated with the pressure and/or the time history of the pressure and/or the time history of a parameter associated with the pressure during and/or after an injection of fuel during a compression phase of the fuel-air mixture.

During or after an injection of fuel, at least a partial evaporation of portions of the fuel takes place in the combustion chamber. This leads on the one hand to a volumetric expansion on account of the now gaseous fuel. On the other hand, the energy expenditure required for the evaporation of portions of the fuel leads to a cooling down of the air situated in the combustion chamber and consequently to a volumetric reduction. In so doing, the volumetric reduction due to the cooling down is the dominating effect. When the combustion chamber volume is specified as a function of the angle of crankshaft rotation, the cooling down causes a reduction in the pressure in the combustion chamber.

How significantly the air cools down on account of the evaporation, therefore how significantly the change in pressure takes place, depends on the characteristics of the fuel, especially on the enthalpy of evaporation and the boiling point, respectively the boiling characteristics. In this respect, typical present-day fuels differ vastly. Thus, ethanol has a fixed boiling point at 78° C., while gasoline displays a boiling range from 25° C. to 215° C. The enthalpy of evaporation lies at 904 kJ/kg for ethanol, while for gasoline it lies in the range of 380 kJ/kg to 500 kJ/kg.

When the pressure or the pressure curve is known in the combustion chamber after an injection of fuel, the fuel or the fuel mixture ratio can be suggested from this information.

The differentiation between the fuels can be determined on the basis of the parameters, which are dependant on the pressure in the combustion chamber, or on the basis of their time history. For this purpose, provision can be made for the composition of the fuel mixture to be ascertained from the torque of the internal combustion engine and/or from the rotational speed of the internal combustion engine and/or from the time history of the rotational speed of the internal combustion engine.

An adequately fast determination of the composition of the fuel mixture on the basis of the pressure, of the pressure curve or of a parameter dependent on said curve can thereby be achieved, in that the composition of the fuel mixture is ascertained from the signal of a compression chamber sensor and/or from the signal of a torque sensor and/or from the signal of a knock sensor and/or from the engine rotational speed signal. The evaluation of the engine rotational speed signal particularly has many advantages because no additional sensor technology is necessary with it, and the correction, respectively adaptation, procedure for an improvement in the accuracy of the signal is already a standard feature in the engine management system. The new application can thus be implemented by a pure software extension. However, also combustion chamber sensors and torque sensors, which offer an additional auxiliary usage for other applications, are increasingly employed in modern internal combustion engines, so that no further significant expenditures are caused by the additional evaluation of the sensor signals for the determination of the fuel mixture ratio. The knock sensor can only be employed if a combustion cycle results after fuel injection because in this instance combustion noises can correspondingly be evaluated.

A change in the fuel composition is only to be expected if a filling of the tank (fueling) has taken place. In this connection, a fast detection of the fuel composition is especially required when initially starting the internal combustion engine after filling the tank (fueling) in order to implement an adaptation of the fuel-delivery control phase to the fuel and to avoid problems in starting and misfires before the fuel adaptation of the closed-loop lambda control achieves a corresponding adaptation. For this reason, provision can be made for the determination of the composition of the fuel mixture to be implemented after a detected filling of the tank (fueling) and/or when starting the internal combustion engine.

In order to implement an evaluation of the pressure or the pressure curve during a compression phase, in which a greatest possible difference exists between the different fuels, provision can be made for the fuel injection to be divided into multiple injection pulses for the determination of the composition of the fuel mixture.

A very large pressure difference between the different fuels than occurs, if the fuel injection into the combustion chamber takes place in air, which has already been compressed. Thus, the fuel injection in a stratified fuel injection can result, for example, shortly before top dead center. In this instance, the compressed air already has a temperature of approximately 100° C.; whereby large parts of the gasoline evaporate, which leads to a significant change in pressure.

Corresponding to an alternative variation of embodiment of the invention, provision can be made for a pilot injection to occur during the compression phase and for the determination of the composition of the fuel mixture to result during and/or after the pilot injection and/or during and/or after the main injection. Provision can be made for a defined small quantity of fuel to be the pilot injection, which is delivered in a compression phase, in which a significant change in pressure is to be expected.

Corresponding to an additional alternative variation of embodiment of the invention, provision can be made for the fuel-air mixture resulting from the pilot injection to be ignited and for the determination of the composition of the fuel mixture to result from the pressure curve during the combustion cycle. In so doing, the fact is utilized that the pressure curve of different fuels significantly varies with regard to ignition. The variation of embodiment can take place in combination with a previous evaluation of the pressure curve during or after the pilot injection in order to increase the evaluative certainty of the method.

According to a particularly preferred variation of embodiment of the invention, provision can be made for a pressure and/or a pressure curve and/or a parameter associated with the pressure to be determined and to be used as a reference parameter for the determination of the composition of an unknown fuel mixture. By means of this adaptation of the combustion chamber pressure curve, respectively the signals derived from it, it is possible to eliminate interfering influences and engine tolerances.

At the same time provision can be made for the composition of the fuel mixture to be determined with the aid of the signal of a lambda probe disposed in an exhaust gas duct of the internal combustion engine and/or by way of a fuel adaptation to adapt the quantity of fuel metered to the internal combustion engine. The fuel adaptation with the aid of the lambda closed loop control is for the most part intended for flex-fuel internal combustion engines and allows for the accurate determination of the fuel mixture ratio, however over an extended timescale. The pressure or the pressure curve can thereby be determined for the mixture ratio, which is determined by way of the fuel adaptation, and deposited as a reference.

An accurate determination of the fuel mixture ratio can thereby be achieved, in that the pressure and/or the pressure curve and/or a parameter associated with the pressure and/or a curve of a parameter associated with the pressure for a known fuel composition and/or during defined operating conditions of the internal combustion engine are ascertained and stored; and in that when determining the composition of the fuel mixture, the associated measured value or the measured values are compared with the stored value or the stored values.

An accurate comparison of the measured values with the stored values can then be achieved if the pressure and/or the pressure curve and/or a parameter associated with the pressure and/or a curve of a parameter associated with the pressure are ascertained and stored as a function of the angle of crankshaft rotation and/or the engine rotational speed and/or the engine temperature and/or the fuel composition and/or the injected fuel quantity. The pressure or the pressure curve is significantly dependent on the parameters mentioned above. The comparison between the previously ascertained reference values and the values measured to determine the fuel mixture ratio is even more accurately possible, the more accurately the conditions when determining the reference values correspond with those when determining the fuel mixture ratio on the basis of the pressure or the pressure curve.

If provision is made for the detection of the composition of the fuel mixture to occur when initially starting the internal combustion engine after filling the tank (fueling) and for a correction of the quantity of fuel delivered to the internal combustion engine during this initial start-up to take place, problems in starting the engine can thus be avoided with certainty even after a significant change in the fuel composition after filling the tank (fueling).

According to a preferred variation of embodiment of the invention, provision can be made for the detection of the composition of the fuel mixture to occur during an overrun phase of the internal combustion engine. An ignition of the air-fuel mixture does not occur during the overrun phase. Thus, steady-state conditions prevail in the combustion chamber without an energy input due to combustion. The temperature change in the combustion chamber by means of the evaporation of the fuel and the change in pressure, which results from it, are not displaced by the energy brought in from the combustion of the fuel in the current or a previous power stroke. This makes a very accurate evaluation of the pressure curve possible and also a corresponding association of the pressure curve to the evaporative energy.

The method particularly allows itself to be advantageously employed for the determination of the composition of a gasoline/ethanol fuel mixture and or for the differentiation between diesel and biodiesel and/or for the differentiation between winter fuel and summer fuel and/or for the determination of the water content in ethanol and/or for the detection of the filling of the tank (fueling) with the wrong type of fuel.

BRIEF DESCRIPTION OF THE DRAWING

The invention is explained below in detail using the example of embodiment depicted in the figure wherein:

FIG. 1 is a graphic depiction of the pressure curve in a combustion chamber of an internal combustion engine when gasoline is injected in comparison with the injection of an ethanol-gasoline mixture.

DETAILED DESCRIPTION

In a graphic depiction, FIG. 1 shows the pressure curve in a combustion chamber of an internal combustion engine when gasoline is injected in comparison with the injection of an ethanol-gasoline mixture.

The angle of crankshaft rotation of the internal combustion engine is depicted on an abscissa 10. An ordinate 11 depicts the pressure in the combustion engine of the internal combustion engine. A first pressure curve 12 shows the pressure in the combustion chamber when an ethanol-gasoline mixture is injected, in this instance in a mixture ratio of 85% ethanol and 15% gasoline, as a function of the angle of crankshaft rotation. A fuel mixture of this composition is also denoted as E85. A second pressure curve 13 shows the pressure in the combustion chamber when gasoline is injected. A third pressure curve 14 corresponds to the pressure in the combustion chamber when no fuel is injected. The curves run congruently up to a region 15. In this region 15 a significant pressure difference however occurs between the first pressure curve 12 and the second pressure curve 13 and the third pressure curve 14. Hence, the pressure difference in the example lies in a magnitude of approximately 3 bar between the first pressure curve 12 and the second pressure curve 13.

Gasoline and ethanol differ considerably in their boiling properties and in their enthalpy of evaporation. In this regard, ethanol has a fixed boiling point of approximately 78° C., while gasoline has a boiling range from 25° C. to 215° C. The enthalpy of evaporation of ethanol amounts to approximately 904 kJ/kg, and that of gasoline lies in a range of 380 kJ/kg to 500 kJ/kg. On the basis of these differences, a difference in the compression curve results.

After an injection of fuel, a partial evaporation of portions of the fuel results in the combustion chamber. This leads on the one hand to a volumetric expansion on account of the now gaseous fuel and on the other hand to a volumetric reduction on account of the cooling down of the air, which is situated in the combustion chamber. The second result, i.e. the cooling down due to evaporation, is thereby the dominant one. Significant differences between gasoline and ethanol are apparent here as a result of the different enthalpies of evaporation.

In the example of embodiment the fuel injection takes place in the form of a stratified fuel injection. An injection of fuel is thereby made shortly before top dead center (OT) into the warm air, which has already been compressed. In this phase the air in the combustion chamber has a temperature of typically around 100° C., whereby a larger portion of the injected fuel can vaporize. This leads to a considerable cooling down of the compressed air and consequently to a drop in pressure in comparison with the third pressure curve 14 when no fuel is injected. The pressure difference between the first pressure curve 12 after injection of E85 and the second pressure curve 13 after injection of pure gasoline amounts to approximately 3 bar in the example of embodiment. Additional mixture ratios between the two fuels: gasoline and ethanol produce pressure curves, which lie between the two. As a result, the pressure curve in the combustion chamber after the injection of fuel provides a direct indication of the fuel mixture ratio. The fuel mixture ratio can accordingly be determined using the pressure curve.

The pressure curve in the combustion chamber can already be determined and compared with stored reference values when starting the engine for the first time after filling the tank (fueling). The fuel mixture ratio can thus already be determined before an initial combustion cycle with an altered mixture ratio; and the quantity of fuel delivered to the internal combustion engine can, for example, can be corrected corresponding to the fuel composition.

The pressure curve can be directly determined by a pressure sensor, for which provision has correspondingly been made. Correlative parameters can, however, also be evaluated with the pressure. Hence, a torque signal or a rotational speed signal of the engine can be evaluated.

The method can be intended for a direct fuel injection or for intake manifold injection systems. In this context the direct fuel injection provides the advantage, in that provision can be made for multiple injections. In so doing, defined least amounts of fuel can, for example, be supplied to the combustion chamber in the form of a pilot injection, and the pressure curve can be accordingly evaluated. Furthermore, it is thereby conceivable for this least amount of fuel to be ignited and additionally for the fuel composition to be suggested from the pressure curve after the ignition.

In order to eliminate as many interfering influences and engine tolerances as possible, it is advantageous to implement an adaptation of the pressure curve in the combustion chamber, respectively the signal derived from it, with known fuel mixture ratios. In order to determine the fuel mixture ratio as a reference value, a lambda probe can thereby be used, which levels out the fuel fluctuations using a known fuel adaptation. The fuel mixture ratio is known by way of this fuel adaptation; however, a settling time is required for this. When a fuel mixture ratio is ascertained in this manner, the pressure curve in the combustion chamber can be stored under defined, reproducible operating conditions, such as the starting, idling or coasting of the internal combustion engine. These pressure curves in the combustion chamber stored for different fuel mixture ratios can be compared with the measured pressure curve after filling the tank (fueling), and the fuel mixture ratio can be derived from this comparison.

The invention claimed is:

1. A method of determining a composition of a fuel mixture from a first fuel and at least a second fuel for operation of an internal combustion engine having at least a combustion chamber, wherein the first fuel and at least the second fuel have different boiling points or different enthalpies of evaporation, the method comprising:

determining a pressure in the combustion chamber;
    determining a parameter associated with the pressure in the combustion chamber;
    determining a time history of the pressure in the combustion chamber;
    determining a time history of a parameter associated with the pressure in the combustion chamber;
    whereby the pressure and the parameter associated with the pressure and the time history of the pressure and the time history of a parameter associated with the pressure in the combustion chamber are determined during an injection of the fuel mixture into the combustion chamber or after an injection of the fuel mixture into the combustion chamber, wherein an injection of the fuel mixture occurs during a compression phase of a fuel-air mixture.

2. A method according to claim 1, further comprising determining the composition of the fuel mixture from a torque of the internal combustion engine, a time history of the torque of the internal combustion engine, a rotational speed of the internal combustion engine, the time history of the rotational speed of the internal combustion engine.

3. A method according to claim 1, further comprising ascertaining the composition of the fuel mixture from a signal of a combustion chamber pressure sensor, a signal from a torque sensor, a signal from a knock sensor, from an engine rotational speed.

4. A method according to claim 1, wherein the fuel mixture composition is determined after a detected filing of a tank or when starting the internal combustion engine.

5. A method according to claim 1, further comprising dividing the injection of the fuel mixture into a plurality of injection pulses when determining the composition of the fuel mixture.

6. A method according to claim 1, further comprising injecting the fuel mixture into the combustion chamber containing pre-compressed air.

7. A method according to claim 1, further comprising determining the composition of the fuel mixture during a pilot injection of the fuel mixture occurring during the compression phase, after a pilot injection of the fuel mixture occurring during the compression phase, after a main injection of the fuel mixture.

8. A method according to claim 7, further comprising igniting the fuel-air mixture resulting from the pilot injection, wherein the determination of the composition of the fuel mixture results from a pressure curve during a combustion cycle.

9. A method according to claim 1, further comprising determining the composition of an unknown fuel mixture utilizing a plurality of reference parameters determined from a known fuel mixture, wherein the plurality of reference parameters include a pressure and a pressure curve and a parameter associated with the pressure of the known fuel mixture.

10. A method according to claim 9, further comprising determining the composition of the unknown fuel mixture with the aid of a signal of a lambda probe disposed in an exhaust duct of the internal combustion engine or by utilization of a fuel adaptation, wherein the fuel adaptation fittingly modifies a fuel quantity metered to the internal combustion engine.

11. A method according to claim 1, further comprising initiating a detection of the composition of the fuel mixture during a start-up of the internal combustion engine after filling a tank, wherein a correction of a fuel quantity supplied to the internal combustion engine occurs during the initial start-up of the internal combustion engine.

12. A method according to claim 1, further comprising storing at least one parameter for a known fuel mixture composition during a defined operating condition of the internal combustion engine, wherein the at least one parameter includes a pressure or a pressure curve or a parameter associated with the pressure or a curve of the parameter associated with the pressure of the known fuel composition, whereby the at least one parameter is compared with an at least one parameter of an unknown fuel mixture for determination of a composition of the unknown fuel mixture.

13. A method according to claim 12, further comprising ascertaining the at least one stored parameter of the known fuel mixture and the unknown fuel mixture as a function of an angle of a crankshaft rotation or an engine rotational speed or an engine temperature or a fuel composition or an injected fuel quantity.

14. A method according to claim 12, wherein a detection of the composition of the fuel mixture occurs during an overrun phase of the internal combustion engine.

15. A method of using an internal combustion engine having at least a combustion chamber to determine a composition of a gasoline/ethanol fuel mixture, to distinguish between a diesel fuel and a biodiesel fuel, to distinguish between a winter fuel and a summer fuel, to determine a water content in ethanol, or to detect a filling of a tank with a wrong fuel added to a tank by the implementation of a method of determining a composition of a fuel mixture from a first fuel and at least a second fuel for the operation of an internal combustion engine having at least a combustion chamber, wherein the first fuel and at least a second fuel have different boiling points or different enthalpies of evaporation, the method comprising: determining a pressure in the combustion chamber; determining a parameter associated with the pressure in the combustion chamber; determining a time history of the pressure in the combustion chamber; determining a time history of a parameter associated with the pressure in the combustion chamber; whereby the pressure and the parameter associated with the pressure and the time history of the pressure and the time history of a parameter associated with the pressure in the combustion chamber are determined during an injection of the fuel mixture into the combustion chamber or after an injection of the fuel mixture into the combustion chamber, wherein an injection of the fuel mixture occurs during a compression phase of a fuel-air mixture.

* * * * *

UNITED STATES PATENT AND TRADEMARK OFFICE
CERTIFICATE OF CORRECTION

PATENT NO. : 7,793,536 B2  Page 1 of 1
APPLICATION NO. : 12/126086
DATED : September 14, 2010
INVENTOR(S) : Schenck Zu Schweinsberg et al.

It is certified that error appears in the above-identified patent and that said Letters Patent is hereby corrected as shown below:

Title page, (75) Inventors: "Meolingen (DE);" should read --Moeglingen (DE);--

Signed and Sealed this
First Day of March, 2011

David J. Kappos
*Director of the United States Patent and Trademark Office*